United States Patent [19]

Blecher et al.

[11] 4,024,857
[45] May 24, 1977

[54] MICRO BLOOD COLLECTION DEVICE

[75] Inventors: Jacob B. Blecher, Fairlawn; Gene W. Tabor, Kinnelon; Charles F. Steinbrink, Jr., Denville; Bruce H. Wand, Morristown, all of N.J.

[73] Assignee: Becton, Dickinson and Company, East Rutherford, N.J.

[22] Filed: Dec. 11, 1975

[21] Appl. No.: 639,858

Related U.S. Application Data

[63] Continuation-in-part of Ser. No. 535,415, Dec. 23, 1974, abandoned.

[52] U.S. Cl. .................. 128/2 F; 23/259; 73/425.4 P; 128/DIG. 5
[51] Int. Cl.² ............................................ A61B 5/14
[58] Field of Search ............... 128/2 F, DIG. 5; 73/425.4 P; 23/259, 232

[56] References Cited

UNITED STATES PATENTS

| 3,539,300 | 11/1970 | Stone | 23/253 |
| 3,545,932 | 12/1970 | Gilford | 23/259 X |
| 3,607,098 | 9/1971 | Strande | 23/259 |
| 3,623,475 | 11/1971 | Sanz et al. | 128/2 R |
| 3,742,934 | 7/1973 | Holbrook et al. | 128/2 F |
| 3,811,326 | 5/1974 | Sokol | 128/2 F X |
| 3,813,223 | 5/1974 | Fleck | 23/259 |
| 3,908,638 | 9/1975 | Porcher et al. | 128/2 F |
| 3,926,521 | 12/1975 | Ginzel | 128/2 F X |

FOREIGN PATENTS OR APPLICATIONS

| 87,197 | 5/1966 | France | 128/2 F |
| 947,908 | 1/1964 | United Kingdom | 128/2 F |

Primary Examiner—Kyle L. Howell
Attorney, Agent, or Firm—Kane, Dalsimer, Kane, Sullivan and Kurucz

[57] ABSTRACT

A micro device for collecting blood from an individual or other blood source into a blood sampler cup, which cup has a removable vented top with a capillary tube passing through the top and contacting or proximate to the inside wall of the cup to deliver blood directly from the blood source to the cup.

12 Claims, 10 Drawing Figures

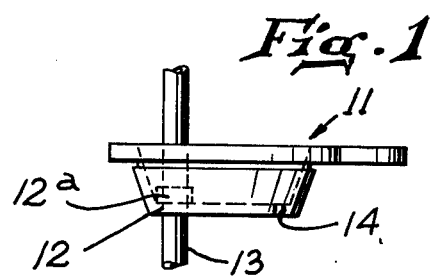
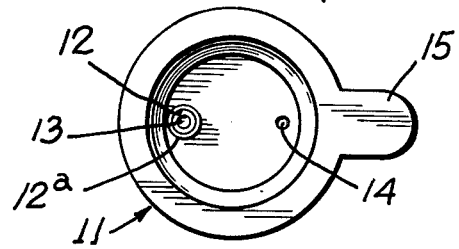
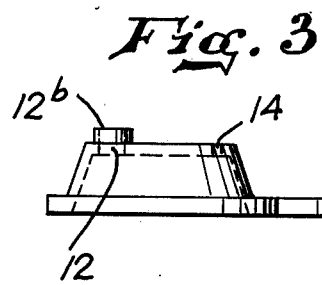
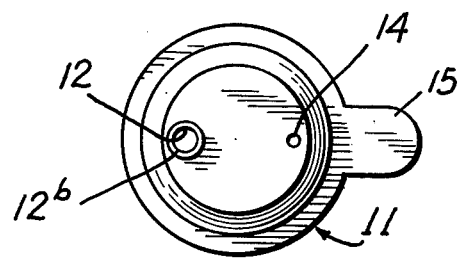
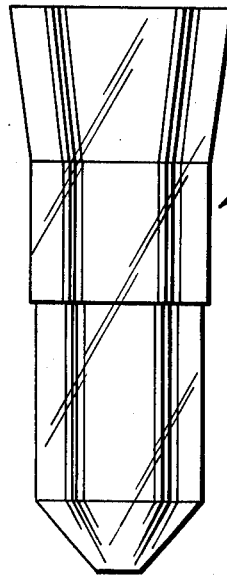
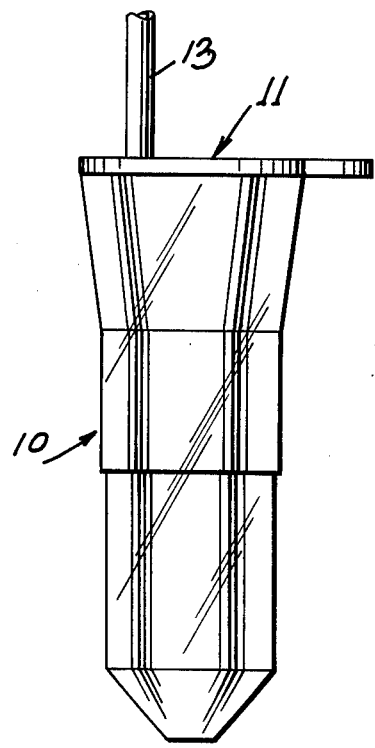
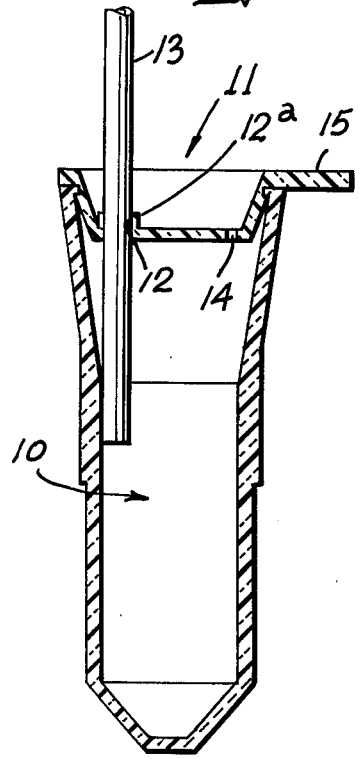

MICRO BLOOD COLLECTION DEVICE

The application is a continuation-in-part of our co-pending U.S. application Ser. No. 535,415, filed Dec. 23, 1974 now abandoned.

BACKGROUND OF THE INVENTION

This invention relates to a micro blood collection device and, more particularly, to a blood sampler cup having a removable vented top fitted with a capillary tube which delivers blood directly from a blood source to the cup.

Recent advances in analytical instrumentation have made it possible to carry out a variety of hematological, chemical and toxicological diagnostic procedures on very small quantities of blood; thereby obviating the need to withdraw venous blood from patients. Instead the smaller qunatities of blood conveniently obtained from capillary blood sources, such as from finger tip or ear lobe, may be used for diagnostic examination.

In co-pending U.S. patent application Ser. No. 400,882, now Pat. No. 3,902,477 granted Sept. 2, 1975 there is described an improved container for collection and storage of capillary blood. Such container meets the requirements for the collection of minute quantities of capillary blood, safe storage thereof without contamination from airborn contaminants, and ready accessibility of the entire specimen when removal is desired. However, the container of that invention is slow to fill. The device of the present invention overcomes such disadvantage and permits obtaining blood samples by directing the blood flow below the upper lip of the cup. The cup can be filled to any desired amount, the normal range being 400-14 1200 microliters.

The following prior art is pertinent but distinguishable from the device of the present invention:

U.S. Pat. Nos. 3,813, 223 — Fleck;
3,623,475 — Sanz et al;
3,607,098 — Strande;
3,545,932 — Gifford;
3,742,934 — Holbrook et al;
3,539,300 — Stone;
French 87,197 (1966) — Goupil
British 947,908 (1964) — Flexible Metal Company, Limited Some of these patents have nothing to do with blood collection (U.S. Pat. Nos. 3,813,223 and 3,607,098). Others require venous pressure for the system to work (French 87,197 and British 947,908) in contrast to the present invention where the initial blood flow requires capillary action and continues to flow due to the force of gravity.

There is no known disclosure in the prior art of the device covered in this application.

SUMMARY OF THE INVENTION

It is an object of the present invention to provide a micro blood collection device which directs a continuous blood flow from a skin puncture in a blood source via capillary action and gravity to a micro sampler cup through a tube leading from the puncture to the interior of the cup.

It is a further object to provide a micro blood collection device which permits obtaining blood samples free of air pockets and red cell contaminations by directing the blood flow below the upper lip of the micro sampler cup.

It is a further object to provide a blood collection device which is simple to operate, economical to manufacture and is efficient and well suited for its intended purpose.

BRIEF DESCRIPTION OF THE DRAWINGS

Other objects and advantages will become apparent from the following description which is to be taken in conjunction with the accompanying drawings, in which:

FIG. 1 is a side elevation of the top for the device of the present invention;

FIG. 2 is a top view of the top of FIG. 1;

FIG. 3 is a side elevation of a modified form of top;

FIG. 4 is a top view of the top of FIG. 3;

FIG. 5 is a side elevation of the blood sampler cup for the device of the present invention;

FIG. 6 is the cup of FIG. 5 with the top of FIG. 1 attached thereto;

FIG. 7 is a sectional view of FIG. 6;

DESCRIPTION OF THE PREFERRED EMBODIMENT

Figure 8:
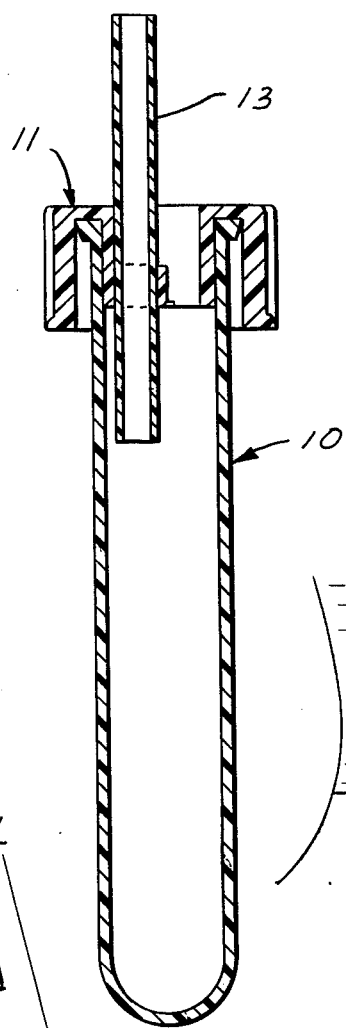
FIG. 8 is a side elevation of a modified form of device of the present invention in which the cup is straight walled and the lateral skirt of the top fits over the outside of the upper end of the cup.

Referring to the drawings, there is shown in FIG. 5 a micro sampler cup 10 which is plastic molded and resembles a centrifuge type tube with a flared top and a convergently tapered bottom. It will be understood that such cup can be straight walled as shown in FIG. 8. Such cup and the top, hereinafter described, should be constructed of materials which will not produce any undesirable chemical reaction with any blood components or any chemicals to be used at a later time in the blood analysis. Such materials may include polyethylene, polypropylene, polyvinylchloride or similar materials.

Adapted to close the cup 10 is a removable vented top 11 (FIG. 1) which is plastic molded and resembles a truncated cone. Such cone has two holes located on the planar surface which truncated said cone. One hole 12 along the outer edge houses a capillary tube 13 and the other hole 14 serves as an air vent (FIGS. 1 and 2). The top is designed to be snapped, force fitted, or otherwise suitably attached to the cup in a conventional manner. The top is provided with a tab 15 to facilitate handling the top and removing it from the cup.

The hole 12 for the capillary tube is provided with a hub 12a (FIG. 1) to provide support for the capillary tube inserted in the hole. In FIG. 1 the hut 12a projects into the well or depression of the top. In FIG. 3 the same form of hub 12b projects outside of the well or depression of the top. Although the top is shown with a well it will be understood that the top can also be formed in flat form with no well, in which case such flat top can be provided with a hub as heretofore described. If such top in either form is made with a thicker wall it may be possible to eliminate the hub as long as there is a rigid fit for the capillary tube so that it will be supported when in use.

The capillary tube is preferably made of glass because it provides a surface over which blood flows freely. However, it will be understood that such capillary tube could be made of plastic in which case it may be necessary to treat the plastic to achieve proper flow of the blood over the plastic surface. If a plastic capillary tube is used, it will be seen that the entire top and capillary tube can be molded as a single piece.

The cup 10 is shown with the top portion tapered inwardly. Thus, when the top 11 with the capillary tube 13 is secured to the upper end of the cup, the tube will project straight downwardly into the cup and is proximate with the interior surface of the tapered side wall of the cup. This occurs by reason of the positioning of the hole for the capillary tube along the outer edge of the top and the taper in the side wall of the cup. However, the side wall of the cup could be straight as shown in FIG. 8, where the capillary tube is positioned at the edge in passing through the top.

When the proximal end of the capillary tube comes in contact with a fluid source, such as a droplet of blood, flow is initiated into the tube if there is positive capillary pressure. Capillary presssure $P_c$ is related to surface tension of the fluid $\sigma$, capillary tube diameter D, and contact angle between fluid and tube material $\theta$; an approximate relation for capillary pressure is:

$$P_c = \frac{4\sigma}{D} \cos\theta \quad \text{(A)}$$

Figure 9:
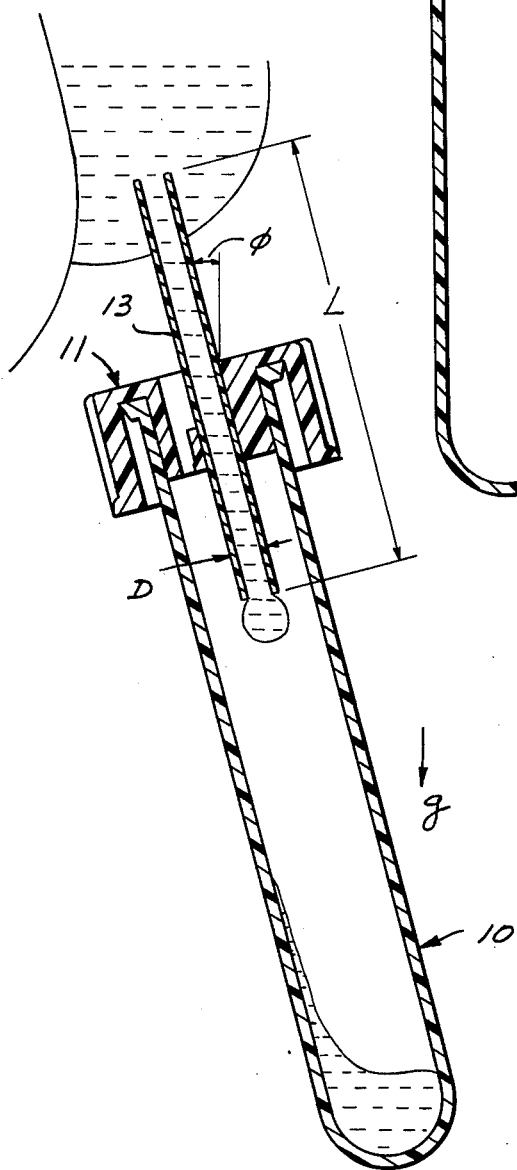
FIG. 9 is a side elevation in section of a blood collection device with a capillary tube extending from a blood source into the central area of a cup showing the formation of a droplet at the inner end of the tube before such droplet falls into the bottom of the cup.
Figure 10:
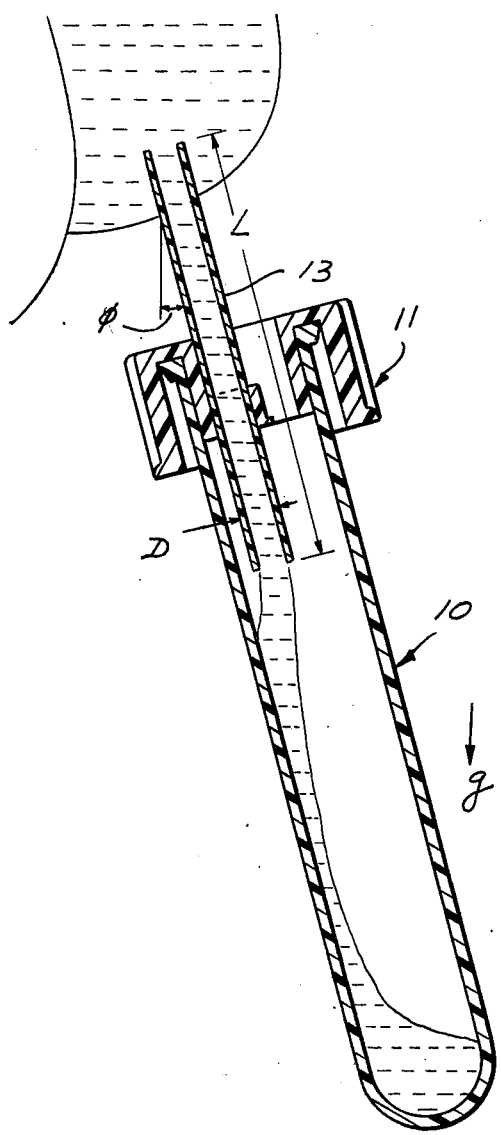
FIG. 10 is a view similar to that of FIG. 9 of the blood collection drive of the present invention showing that, after the formation of the first droplet, the blood will flow continuously by gravity from the blood source to the interior side wall of the cup.

Capillary pressure is positive if the fluid "wets" the capillary tube material (i.e., if contact angle $\theta$ is less than 90°). Flow is not initiated into tubes which the fluid does not wet (i.e., capillary pressure $P_c$ is negative since contact angle $\theta$ is greater than 90°). Once flow is initiated into the tube due to positive capillary pressure, it will continue due to the force of gravity, provided that the distal end of the tube is lower than the proximal end. When the flow reaches the distal end of the capillary tube, two possible flow regimes exist, which are illustrated in FIGS. 9 and 10. In FIG. 9 a droplet forms at the distal end of the tube, and the pressure behind the droplet reaches a maximum of $4\sigma/D$. Thus, in order for flow to continue (neglecting momentum effects), $$\rho g L \cos\phi \geq \frac{4\sigma}{D}$$

or $$L \cdot D \geq \frac{4\sigma}{\rho g \cos\phi} \quad \text{(B)}$$

where L is the length of the capillary tube, $\rho$ is the fluid density, g is the acceleration due to gravity, and $\phi$ is an arbitrary angle which the capillary tube makes with the vertical. If relation (B) for L·D is satisfied, drops will grow to an unstable size and fall off. Drop flow will be continuous, but it will also be slow and non-uniform. In FIG. 10, the droplet which formed at the distal end of the capillary tube came into contact with the wall of the collection cup. Since the drop can run down the wall of the collection cup, flow is faster, and uniform because there are no surface tension related forces to retard flow. The mass flow rate is given by:

$$\dot{M} = \frac{\rho^2 \pi D^4 g}{128 \mu} \cos\phi \quad \text{(C)}$$

where $\mu$ is the viscosity of the fluid and blood flow will continue in a constant manner.

The flow of the fluid (blood) from a source to the collection cup through a capillary tube is described in detail in the above paragraph. The present invention has been designed such that the materials used permit flow initiation through capillary action (i.e. $P_c > 0$ from equation (A)) and such that capillary tube dimensions permit continuous flow (i.e., the relation for L·D from equation (B) is satisfied). By positioning the capillary tube near the wall of the collection cup, the flow into the collector (given by equation (C)) is fast and uniform, and blood flows continually into the cup. The vent hole 14 is placed opposite the capillary tube hole in the top to provide for air displacement and hence allow for a free flowing blood sample. The top provides for obtaining blood samples (serum or plasma) free of red cell contamination by directing the blood flow below the upper lip portion of the cup, thereby eliminating red cell adherence to interior wall.

When the volume of the blood sample required has been reached, the top is removed from the cup, a cap is placed on the cup and the cup and contents are then placed in a centrifuge and spun downward and the serum or plasma is removed.

Although reference has been made herein to blood from an individual, it should be understood that the device is equally useful for obtaining blood from animals and the term "blood source" used herein encompasses individuals and animals.

Thus among others, the several aforenoted objects and advantages are most effectively attained. Although a somewhat preferred embodiment of the invention has been disclosed and described in detail herein, it should be understood that this invention is in no sense limited thereby and its scope is to be determined by that of the appended claims.

Having thus described the invention, what is claimed is:

1. A micro device for collecting blood from a blood source comprising:

a blood sampler cup for receiving and holding the said blood, said cup being closed at one end and open at the other end;

a removable top removably secured to and closing the open end of the said cup;

a vent into the said cup;

a capillary tube of substantially uniform internal diameter throughout its length projecting through the said top into the cup to convey the said blood from the blood source to the said cup, the said capillary tube being so positioned that the end of tube within the cup will be proximate to the interior surface of the side wall of the cup;

whereby the blood can flow directly from the blood source through the capillary tube to the interior side wall of the cup along a contiguous path, the flow of the blood into the tube is initiated under positive capillary pressure essentially defined by the equation $$P_c = \frac{4\sigma}{D} \cos \theta \quad (A)$$

where $P_c$ equals capillary pressure, $\sigma$ is surface tension of the fluid, D is capillary tube diameter and $\theta$ is the contact angle between the fluid and the tube material, flow of blood through the tube is continued under the influence of the force of gravity such that a droplet of blood forms at the distal end of the tube experiencing the pressure $4\sigma/D$ and satisfies the relationship $$L \cdot D \geq \frac{4\sigma}{\rho g \cos \phi} \quad (B)$$

where L is the length of the capillary tube, $\rho$ is the fluid density, $g$ is the acceleration due to gravity, and $\phi$ is an arbitrary angle which the capillary tube makes with the vertical, the droplet forming at the distal end adapted to engage with the interior surfaces of the cup and flow will continue in a constant manner according to the formula $$\dot{M} = \frac{\rho^2 \pi D^4 g}{128 M \mu} \cos \phi \quad (C)$$

where $\dot{M}$ is the mass flow rate and $\mu$ is the viscosity of the fluid.

2. The device of claim 1 wherein the said top is provided with a first hole with a hub to receive the capillary tube and substantially rigidly support the said tube.

3. The device of claim 2 wherein the said top is provided with a second hole to serve as a vent for the cup.

4. The device of claim 1 wherein the side wall of the said cup is tapered inwardly toward the bottom to facilitate the end of the said capillary tube projecting into the cup being proximate to the interior surface of the side wall of the said cup.

5. The device of claim 1 wherein the said top is provided with a well in the form of a truncated cone with first and second holes positioned on the planar surface which truncated said cone.

6. The device of claim 1 wherein the said cup and said top are formed of plastic.

7. The device of claim 1 wherein the said cup and said top are formed of a material which is compatible with blood components or any chemicals to be used at a later time in the analysis of said blood sample contained within.

8. The device of claim 7 wherein the said cup and said top are formed of a material selected from the group polyethylene, polypropylene and polyvinylchloride.

9. The device of claim 1 wherein the said capillary tube is so positioned that the end of the tube within the cup is in contact with the interior surface of the side wall of the cup.

10. The device of claim 1 wherein the said top is in the form of a cup having a skirt which is adapted to fit over the outside upper end of the cup.

11. The device of claim 1 wherein the capillary tube and top are formed of plastic molded into a single piece.

12. The method of collecting blood from a blood source with a micro device having a blood cup open at one end, a top closing the open end of the cup, and a capillary tube of substantially uniform internal diameter throughout its length projecting through the top into the cup with the end of the tube within the cup being proximate to the interior surface of the side wall of the cup, comprising:

providing a blood source;

bringing the end of the capillary tube outside of the cup into contact with the blood source to initiate the flow of blood into the tube by capillary action in accordance with the equation $$P_c = \frac{4\sigma}{D} \cos \theta \quad (A)$$

where $p_c$ equals capillary pressure, $\sigma$ is surface tension of the fluid, D is capillary tube diameter and $\theta$ is the contact angle between the fluid and the tube material;

positioning the device so that the blood will flow through the tube by gravity to form an initial droplet at the end of the tube within the cup which droplet experiencing the pressure $4\sigma/D$ and satisfys the relationship $$L \cdot D \geq \frac{4\sigma}{\rho g \cos \phi} \quad (B)$$

where L is the length of the capillary tube, $\rho$ is the fluid density, $g$ is the acceleration due to gravity, and $\phi$ is an arbitrary angle which the capillary tube makes with the vertical, and which droplet will come into contact with the interior surface of the side wall of the cup and flow will continue in a constant manner according to the formula $$\dot{M} = \frac{\rho^2 \pi D^4 g}{128 M \mu} \cos \phi \quad (C)$$

where $\dot{M}$ is the mass flow rate and $\mu$ is the viscosity of the fluid;

whereby blood will then flow continuously from the blood source through the tube to the interior side wall of the tube along a contiguous path.

* * * * *